United States Patent [19]

Halasz

[11] 4,197,941
[45] Apr. 15, 1980

[54] SANITARY KIT PACKAGE

[75] Inventor: Peter R. Halasz, Los Angeles, Calif.

[73] Assignee: Bergen-Brunswig Corporation, Los Angeles, Calif.

[21] Appl. No.: 938,832

[22] Filed: Sep. 1, 1978

[51] Int. Cl.² .................... B65D 85/62; B65D 77/26; B65D 77/28

[52] U.S. Cl. .................... 206/216; 4/144.1; 206/45.14; 206/194; 206/434; 229/40

[58] Field of Search .................. 206/45.14, 45.19, 168, 206/194, 432, 434, 216; 229/40, 52 BC; 220/416; 4/144.1

[56] References Cited

U.S. PATENT DOCUMENTS

| 3,002,609 | 10/1961 | Batkin | 206/45.14 |
| 3,159,273 | 12/1964 | Schecterson et al. | 206/45.19 |
| 3,168,963 | 2/1965 | Wolowicz | 206/194 |
| 3,298,513 | 1/1967 | Krooss et al. | 206/434 |
| 3,693,788 | 9/1972 | Oglesbee | 206/432 |
| 3,777,739 | 12/1973 | Raitto | 4/144.1 |
| 3,878,571 | 4/1975 | Seeley | 4/144.1 |

Primary Examiner—William T. Dixson, Jr.
Attorney, Agent, or Firm—G. Donald Weber, Jr.

[57] ABSTRACT

There is provided a unique tray or package for presenting a sanitary (sterile) container. The package is arranged so that the container and associated parts of the kit are presented in a specific and sequential manner so that a prescribed utilization of the container and associated apparatus is achieved and a sterile condition is maintained.

14 Claims, 3 Drawing Figures

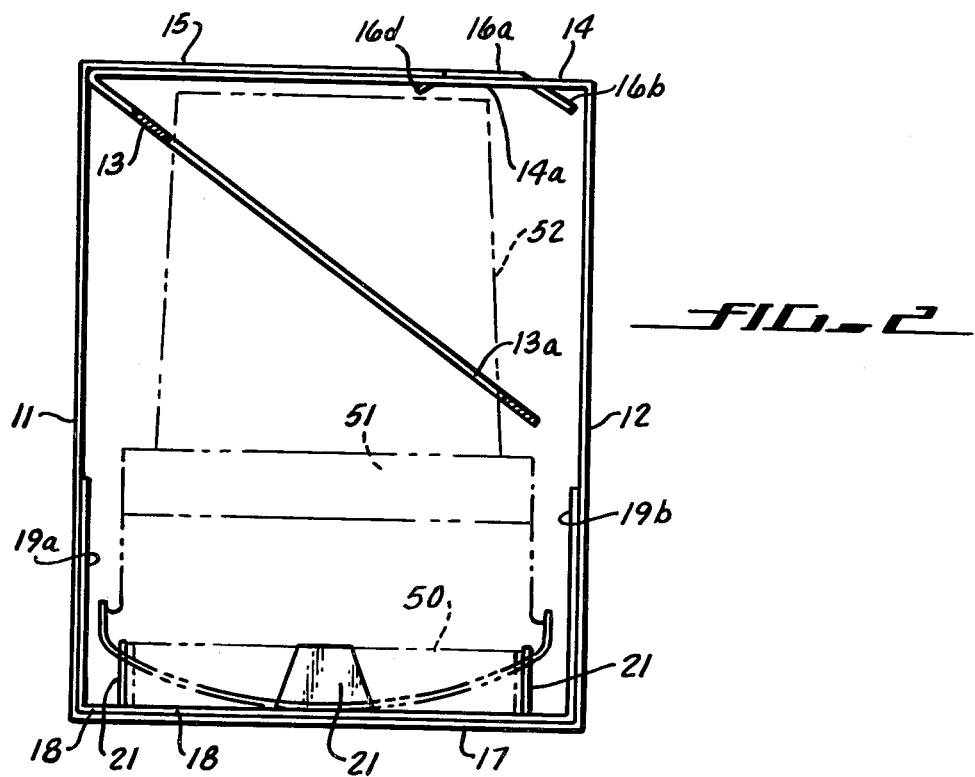
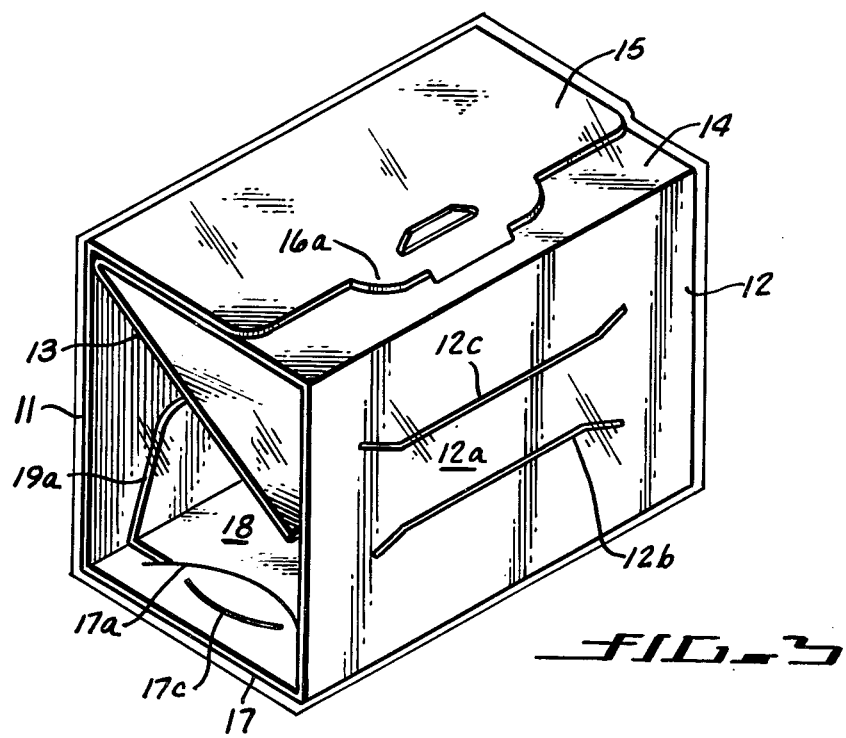

SANITARY KIT PACKAGE

BACKGROUND

1. Field of the Invention

This invention is directed to a packaging concept, in general, and a packaging concept which is directly related to an aseptic packaging arrangement, in particular.

2. Prior Art

In performing many medical analyses or diagnoses, it is necessary or desirable to have a urine specimen from the patient. There are several methods of obtaining urine specimens. One such method is through the use of the "mid-stream" collection procedure. In the midstream method of obtaining the specimen the patient monitors and completes the specimen taking essentially unattended by a physician or other medical professional. However, if adequate care and control is not maintained, the specimen can become contaminated, usually through the carelessness, neglect or ignorance of the patient. That is, the patient will frequently handle the specimen container in a manner such as by contacting the specimen container with the patient's hands or the like which causes the container to no longer be sterile. Consequently, it is highly desirable to provide a kit or suitable arrangement for pesenting the specimen container as well as utilization instructions in a sequential manner which is substantially controlled so that the patient cannot inadvertently contaminate the container. Therefore, by providing a package which controls the access to the various parts of the kit and the specimen container so that a sequential utilization is established, a more controlled method of obtaining an uncontaminated specimen is provided.

There are known in the art, several types of packages which are directly related to aseptic or sanitary packaging conditions. Some of these sanitary packaging arrangements are directed at "mid-stream" collection of urine wherein aseptic urine specimens are obtained. The known mid-stream collection devices or kits currently on the market comprise a container with either a funnel or a handle associated therewith. Of the known devices on the market, all incorporate one or more shortcomings or weaknesses. For example, in the known catch kits which use rigid funnels, the container is packaged in a closed, sealed box or carton which does not permit the patient or the medical professional to view the apparatus for preliminary instructions. In addition, the cap for ultimately closing the container (as well as the funnel) can be fairly easily contaminated by the patient.

Another kit in this general market also uses a funnel which is packaged in a container which is at least partially transparent. However, the package is frequently difficult to open which tends to cause the patient to contaminate the container. In addition, the package is arranged in such a manner that the aseptic lid is frequently jarred loose within the package and is, therefore, easily contaminated by the patient, also. Moreover, because of the structure of the package, it is difficult to stack in storage.

SUMMARY OF THE INVENTION

The invention relates to an organized mid-stream collection kit which is simple and effective for use by a patient to provide an aseptic specimen. The unique tray folds out to present a specimen container and pre-attached funnel in an inverted position. The package comprises a plurality of panels which are interrelated to securely support and retain the specimen container and to present the container to a user in a specified manner. Also, the container lid is located beneath the inverted funnel with the threaded portion protected. The panels of the tray interlock to all parts of the container kit in a predetermined relationship. The aseptic specimen container is presented in a controlled fashion wherein contamination is virtually impossible in an inadvertent action. The entire package is cased in polypropylene film to maintain the aseptic condition. In addition, the package is stackable and shippable in standard commerce and storage areas.

BRIEF DESCRIPTION OF THE DRAWINGS

FIG. 2 is a cross-sectional view of the tray assembled and retaining a container.

FIG. 3 is a perspective view of the fully assembled package including the protective film.

DESCRIPTION OF A PREFERRED EMBODIMENT

Figure 1:
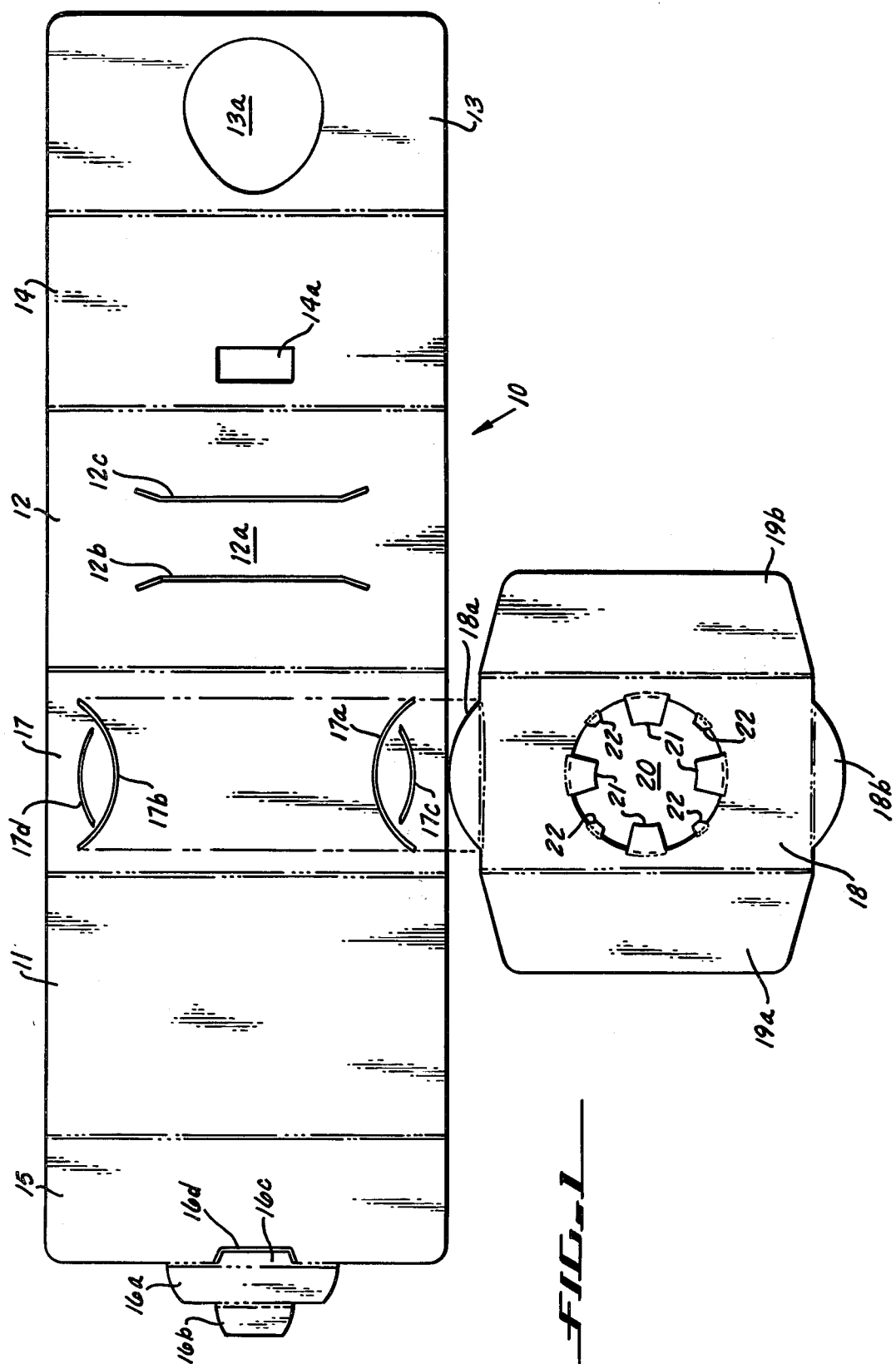
FIG. 1 is a plan view of the blank which is used to make the tray.

Referring now to FIG. 1, there is shown a plan view of the two part blank used to produce the tray covered by the instant invention. The major or outer portion 10 of the tray comprises six panels which are connected in series at prescored edges. Side panel 11 is basically rectangular and is arranged to include a place for instructions to be printed thereon. The instructions can, in a preferred embodiment, include multi-language and diagrammatic instructions. Opposite side panel 12 is of substantially the same size and configuration as side panel 11. However, side panel 12 includes a pair of slits 12B and 12C therein to form strap 12A into which packages of towellettes, ID data and any other special instructions or components can be inserted. The interior locking panel 13, which will be discussed hereinafter, includes a large aperture 13A therein. The size and shape of the aperture is determined by the type of container or other object to be mounted and secured in the sterile tray.

Panels 14 and 15 interact to form a locking top panel. Panel 14 forms the actual top panel and includes a substantially rectangular aperture 14A therein. Panel 15 is approximately half as wide tab as top panel 14 and includes relatively wide portion 16A, relatively narrow portion 16B and a slot 16D therein which defines tab 16C. Tab 16 interacts with aperture 14A in panel 14 to form a locking arrangement which is not readily opened or jarred during shipping or handling. However, the tab is relatively easily opened by a patient or user.

Bottom panel 17 includes a pair of slits 17A and 17B at opposite ends thereof. The slits are arcuate in shape and approximately a one-third portion of a circle. In addition, arcuate slits 17C and 17D are provided in the tabs defined by slits 17A and 17B. Slits 17A and 17B are in the reverse orientation relative to slits 17C and 17D.

The separate insert which is utilized with the tray comprises bottom panel 18 and includes tabs 18A and 18B which project from the opposite ends thereof. These tab projections are inserted into the slits 17A and 17B in panel 17 of tray 10. Tabs 18A and 18B serve to lock panel 18 into position and, also to protect the ends of funnel 51 described hereinafter. In addition, panel 18 includes a large aperture 20 which has plurality of tabs 21 projecting inwardly thereto. Each of the tabs 21 is joined to panel 18 at the base thereof which is scored for relatively easy folding in an upwardly manner, as will become apparent hereinafter. Likewise, a plurality of relatively small tabs or ears 22 extend inwardly into aperture 20 to grasp the container lid as described hereinafter. The side panels 19A and 19B which are joined to panel 18 are substantially rectangular or trapezoidal (as shown) although the configuration thereof is not critical to the invention. Side panels 19A and 19B are, however, of appropriate size and shape to protect the side edges of funnel 51.

Referring now to FIG. 2, there is shown a cross sectional view of the tray when assembled and including therein a specimen container. In the assembly procedure, tabs 21 are folded upwardly, out of the plane of the drawing, and cap 50 is inserted into aperture 20 with the outer edges exposed and the inner threaded edges of the cap disposed below panel 18. Cap 50 is contained securely in panel 18 as a combined result of friction or force fit produced by tabs 21 and 22. The frictionally secured cap 50 and the separate blank are combined with blank 20 by inserting tabs 18A and 18B into slots 17A and 17B in panel 17, respectively. The interaction of the tabs and slits is such that panel 18 is quite securely interlocked with blank 10 wherein cap 50 is maintained such that only the outer surface is available to be grasped by a user of the product.

Next, the specimen container which includes the funnel 51 and the actual container 52 are assembled. That is, container 52 is threadedly engaged with funnel 51 to form a single unit. The funnel is placed over cap 50 and the ends of the funnel trough are inserted into slits 17A and 17B and, simultaneously, into slits 17C and 17D whereby the funnel is secured to tray 10. It is clear, that cap 50 is now covered over and is inaccessible to the user until the specimen container including cup 52 and funnel 51 have been removed. Moreover, funnel 51 is secured by the tabs in panel 17 such that only the outer surface of container 52 (and funnel 51) are available to the user. In as much as the specimen does not contact any of these surfaces, contamination is still prevented. At this time, panels 19A and 19B are folded upwardly to provide additional support for the funnel and cup combination.

Next, the towellette packages, ID label and any other suitable paraphenalia are inserted into slits 12B and 12C in panel 12 and maintained therein under strap 12A.

At this point, panels 11 and 12 are folded upwardly to form the side panels of the package. At approximately this time, panel 13 is folded back against panel 14. Panel 14 is then folded over at approximately 90 degrees relative to side panel 12. Panel 13 is then released wherein the aperture 13A slips around cup 52 to securely mount the cup and prevent it from moving during handling. Thus, panel 13, after release, forms approximately a 30 degree angle with top panel 14. This particular angle is a function of the specific configuration of the aperture 13A and the outer configuration of the cup 52. With these panels now in place, panel 15 is folded over panel 13, essentially parallel to and substantially in contact therewith.

At this point, tab 16 is flexed downwardly at the common edge with panel 15. Thus, tab 16C is placed in engagement with the edge of aperture 14A in panel 14. Next, tab 16B is flexed at the common edge with tab 16 wherein tab 16B is inserted into aperture 14A in panel 14. Tabs 16D and 16B form positive interlocks with the edges of aperture 14A in panel 14. Tab 16A is sufficiently large to encompass the width of aperture 14A thereby assisting in the interlocking arrangement.

Referring now to FIG. 3, there is shown a perspective view of the fully assembled tray and container apparatus wrapped in a suitable outer film or layer. In a preferred embodiment, the outer film is polypropylene film which is relatively tough and durable but is also transparent. The film is placed around the package and sealed by a suitable thermal sealing element wherein the package is now fully sealed but the inner parts are fully visible to the user. The entire apparatus is then placed in a suitable sterilization apparatus such as is known in the art which applies a relatively low temperature through the kit in an ethylene atmosphere which is a known sterilizing technique. Thus, the sealed package is sterilized.

Once the package has been assembled as is shown in FIG. 3, a totally sanitary, aseptic unit is maintained and contained therein. For the patient to utilize the collection apparatus, the reverse unpackaging is followed. That is, the sterile, aseptic package is opened by first removing the polypropylene film. Thereafter, tab 16 (which may include a legend to indicate lifting of the tab) is lifted so that tab 16B is removed from aperture 14A whereupon tab 16D becomes readily releasable from aperture 14A, also. In this condition, panels 15 and 11 fall to the generally horizontal position thereby exposing the directions and instructions to the user. Once the user has read the instructions, panel 13 is lifted off cup 52 wherein panels 12, 13 and 14 are now disposed in a horizontal position. Of course, panel 13 can be disengaged from cup 52 substantially concurrently with the removal of panels 11 and 15. Thus, the towellettes, ID label and other paraphenalia at panel 12 are exposed and readily accessible to the user or patient. The proper procedures are followed with regard to this material. Thereafter, the specimen container is removed from the tray by grasping cup 52 and removing funnel 51 from the edges of the tabs in panel 17. After the specimen has been placed in cup 52, the funnel 51 can be unscrewed from the cup and disposed of in any suitable manner. At this point, the contamination or not of funnel 52 is relatively immaterial. Thereafter, cap 50 which has only been exposed after removal of the funnel/cup apparatus, is removed by grasping the cap and pulling it forcibly out of the aperture in panel 18. Again, only the outer surfaces of cap 50 are touched by the patient or user. Consequently, no contamination is inadvertently placed on the inner surface of cap 50. Cap 50 is then screwed onto cup 52 thereby maintaining the specimen in the cup in an uncontaminated condition.

Thus, there is shown and described an organized tray which requires that the user or patient follow instructions explicitly and, thereby, prevents contamination of the specimen container. In addition, the package protects and secures the components in such a manner that they will not fall apart and be inadvertently, exposed to contamination v hen the patient takes them out of the package. Along the same line, because of the package construction, only the outer surfaces of the container apparatus are readily available to the user, which again improves the contamination-avoidance aspect. The package provides transparent ends through which a patient can observe the apparatus and be preliminarily instructed by any professional personnel. Of course, while the invention has been described in terms of a urine specimen container, the package can be directed to other types of specimen containers if so desirable. Moreover, the package, when fully assembled is a relatively neat and geometrically regular package which readily lends itself to stackability, storage and transporation. While those skilled in the art may conceive modifications to the instant invention, any such modifications which fall within the purview of this description are intended to be included as well. The description is intended to be illustrative only and not limitative. The scope of the invention is limited only by the scope of the claims appended hereto.

Having thus described a preferred embodiment of the instant invention, what is claimed is:

1. In combination,
   first and second blanks which can be interconnected,
   said first blank including a major panel with an aperture therein for receiving a first component,
   said second blank including a first panel having slots for receiving said major panel of said first blank and a second component which covers said first component,
   second and third panels joined to said first panel to form sides of said unit,
   top panel means including locking means for joining said second and third panel means together, and
   securing panel means which depends from said top panel means in order to engage and secure said second component.

2. The combination recited in claim 1 wherein, said major panel of said first blank includes tab means at the ends thereof for insertion into said slots in said first panel of said second blank.

3. The combination recited in claim 2 wherein,
   said slots and said tab means comprise interaction arcuate configurations.

4. The combination recited in claim 2 including,
   trapezoidal side panels joined to the opposite side edges of said major panel.

5. The combination recited in claim 1 wherein,
   said major panel of said first blank includes tab means projecting into said aperture to engage said first component.

6. The combination recited in claim 5 wherein,
   at least one of said tab means is adapted to be folded upwardly with respect to said major panel.

7. The combination recited in claim 1 wherein,
   at least one of said second and third panels includes slots therein for receiving additional components.

8. The combination recited in claim 1 wherein,
   said top panel means includes a top panel connected between said securing panel and one of said second and third panels, and
   a tab panel with locking tabs thereon,
   said locking tabs arranged to engage a locking aperture in said top panel.

9. The combination recited in claim 8 wherein,
   said locking tabs include first and second tabs for insertion into said locking aperture,
   said first tab extending beyond the edge of said tab panel,
   said second tab formed at the edge of said tab panel 10. The combination recited in claim 8 wherein,
    said first panel and said top panel have substantially the same size and configuration, and
    said second and third panels have substantially the same size and configuration.

11. The combination recited in claim 1 including,
    sealing means surrounding the assembled package constructed from said first and second blanks.

12. The combination recited in claim 1 wherein,
    said sealing means comprises a polypropolene film.

13. The combination recited in claim 1 wherein,
    said first component comprises a funnel associated with a container, and
    said second component comprises a lid for said container.

14. The combination recited in claim 1 wherein,
    said first blank includes side panels connected to the sides of said major panel for protecting both said first and second components.

* * * * *